United States Patent [19]

Metlesics et al.

[11] 3,931,217
[45] Jan. 6, 1976

[54] 2,3-DIHYDRO-5-ALKOXY-5-PHENYL-5H-IMIDAZO[2,1-A]ISOINDOLES

[75] Inventors: Werner Metlesics, Clifton; Leo Henryk Sternbach, Upper Montclair, both of N.J.

[73] Assignee: Hoffmann-La Roche Inc., Nutley, N.J.

[22] Filed: May 6, 1974

[21] Appl. No.: 467,428

Related U.S. Application Data

[60] Division of Ser. No. 639,315, May 18, 1967, which is a continuation-in-part of Ser. No. 626,965, March 30, 1967.

[52] U.S. Cl. ... 260/309.6; 260/239 BC; 260/251 R; 260/591; 260/618 B; 424/244; 424/251; 424/273
[51] Int. Cl.² .................................. C07D 235/02

[58] Field of Search .................................. 260/309.6

[56] References Cited
UNITED STATES PATENTS
3,444,181    5/1969    Houlihan .................. 260/309.6

*Primary Examiner*—G. Thomas Todd
*Attorney, Agent, or Firm*—Samuel L. Welt; Bernard S. Leon; William G. Isgro

[57] ABSTRACT

Novel 2[2-(1,3-diazacycloalk-2-enyl)]benzophenone compounds and novel 1,3-diazacycloalkenyl[2,1-a]isoindole compounds having useful analgesic and psychostimulant properties are prepared inter alia by condensation of o-benzoylbenzaldehydes with aliphatic diamines.

2 Claims, No Drawings

2,3-DIHYDRO-5-ALKOXY-5-PHENYL-5H-IMIDAZO[2,1-A]ISOINDOLES

RELATED APPLICATIONS

This is a division of application Ser. No. 639,315 filed May 18, 1967, which in turn is a continuation-in-part of U.S. Patent application Ser. No. 626,965, filed Mar. 30, 1967.

BRIEF SUMMARY OF THE INVENTION

This invention relates to a novel class of 2[2-(1,3-diazacycloalk-2-enyl)]benzophenones and novel 1,3-diazacycloalkenyl[2,1-a]isoindoles, novel processes and intermediates for the preparation of said novel products and derivatives thereof and to the use of said novel compounds as pharmaceuticals. More particularly, the invention in its product aspect relates to novel compounds of the formula

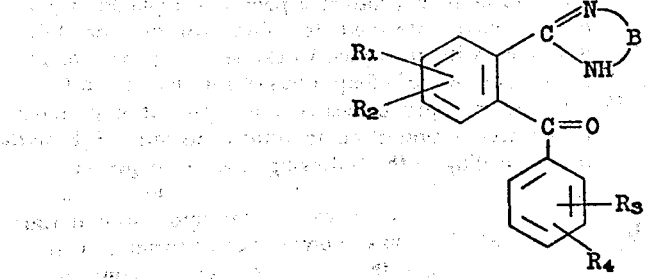

wherein B represents an alkylene chain of 2 to 4 carbon atoms in which one or more of the hydrogens can be replaced by lower alkyl; and $R_1$, $R_2$, $R_3$ and $R_4$ are each independently selected from the group consisting of hydrogen, halogen, lower alkyl, lower alkoxy, hydroxy and trifluoromethyl and pharmaceutically acceptable acid addition salts thereof.

Compounds of formula I can undergo a prototropic shift to form compounds of the formula

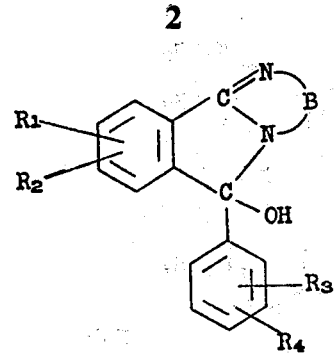

wherein $R_1$, $R_2$, $R_3$, $R_4$ and B each have the same meaning as hereinabove.

The invention includes both tautomeric isomers as well as mixtures thereof. Tautomeric mixtures can be represented schematically as

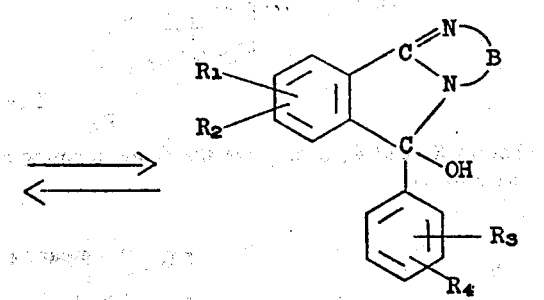

wherein $R_1$, $R_2$, $R_3$, $R_4$ and B each have the same meaning as hereinabove.

DETAILED DESCRIPTION

In one product aspect this application pertains to the novel compounds of formulas I and II and derivatives thereof. Of particular interest are the compounds of formulas I and II wherein B represents the group $$\begin{matrix} R_5 & R_6 \\ | & | \\ -CH-CH- \end{matrix}$$

and $R_5$ and $R_6$ are each independently hydrogen or lower alkyl, i.e., compounds of the formulas

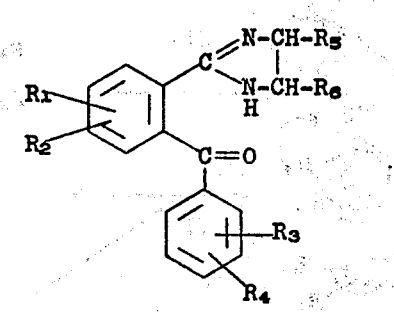 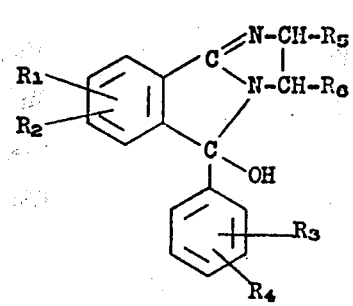

wherein $R_1$, $R_2$, $R_3$ and $R_4$ each have the same meaning as hereinabove; and $R_5$ and $R_6$ are each independently hydrogen or lower alkyl and their pharmaceutically acceptable acid addition salts and tautomeric mixtures.

Compounds of formulas I-a and II-a wherein $R_1$, $R_3$, $R_5$ and $R_6$ are each hydrogen, i.e., compounds of the formulas

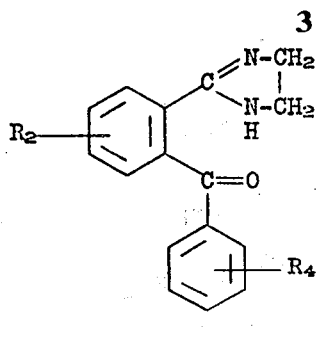

I-b

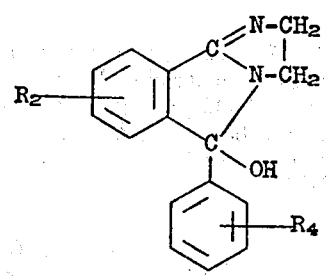

II-b wherein R₂ and R₄ each have the same meaning as hereinabove and their pharmaceutically acceptable acid addition salts and tautomeric mixtures constitute a preferred group.

In another product aspect this application pertains to the mixed ethers obtained from compounds of formula II and lower alkanols, i.e., compounds of the formula

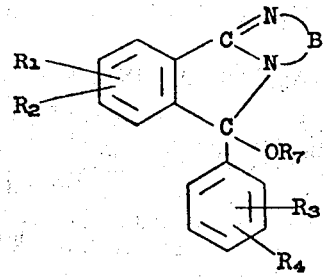

II-d wherein $R_1$, $R_2$, $R_3$, $R_4$ and B each have the same meaning as hereinabove; and $R_7$ is lower alkyl.

In still another product aspect this application pertains to novel intermediates which will be more fully described with reference to the several processes for the preparation of compounds of formulas I and II.

In one of its process aspects this application pertains to the preparation of compounds of formulas I, II and II-d according to the following reaction sequence.

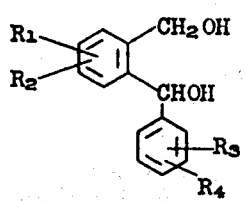

V

↓

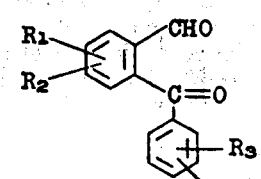

IV

↓

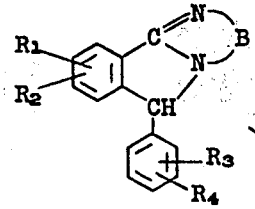

III

⟶

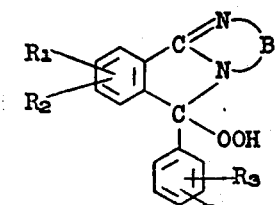

II-c

↓

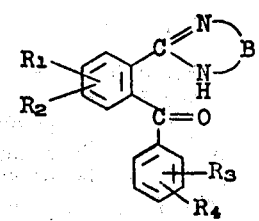

I

⇌

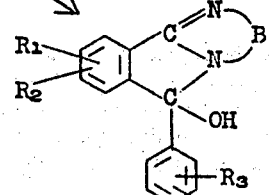

II

↓

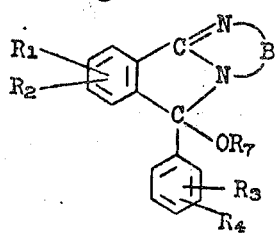

II-d wherein $R_1$, $R_2$, $R_3$, $R_4$, $R_7$ and B each have the same meaning as hereinabove.

The diol starting materials of formula V are known compounds or are readily obtainable in analogy to the preparation of the known compounds. The diol starting materials can be readily converted to the dicarbonyl intermediates of formula IV by oxidation techniques which are known per se such as, for example, using selenium dioxide and the like, as the oxidizing agent or by employing other oxidizing systems such as chromium trioxide in pyridine.

Treatment with an oxidizing agent can be conveniently carried out in an organic solvent such as, for example, dimethylformamide, dimethylsulfoxide; hydrocarbon solvents such as benzene, toluene; alkanols, e.g., the lower alkanols, methanol, ethanol, etc.; acetic acid and the like. The oxidation reaction is preferably carried out at an elevated temperature suitably at a temperature between about room temperature and about 150°C.

The intermediates of formula IV are themselves novel compounds and thus also constitute part of this invention. The intermediates of formula IV are readily condensed with diamines of the formula $$NH_2—B—NH_2 \qquad XII$$

wherein B has the same meaning as hereinabove by mixing the components or by reacting them in the presence of an organic solvent such as benzene, toluene; alcohols such as lower alkanols and the like. The condensation is conveniently carried out at room temperature or above, preferably at a temperature between about 20°C. and 150°C. Alternatively, the diamine reactant of formula XII can be employed as a salt thereof in which case the reaction is conducted by heating the mixture of reactants to a melt.

The reaction products, i.e., the compounds of formula III, can be readily oxidized, for example, by treatment with an oxidizing agent such as hydrogen peroxide or by exposure to gaseous oxygen at room temperature to give the peroxides of formula II-c which are readily reduced to the corresponding end products. The oxidation is conveniently carried out in an organic solvent such as alcohols, dimethylformamide, etc. at room temperature. Higher or lower temperatures, e.g., between about 20°C. and 100°C., can also be employed.

Since the peroxide intermediates readily undergo reduction, the reaction mixture obtained upon treatment of a compound of formula III with an oxidizing agent will ordinarily contain the end products along with the peroxide intermediate of formula II-c. Complete reduction of the peroxide can be accomplished without separating it from the reaction mixture and, in a preferred embodiment, the oxidation product is submitting directly to treatment with a reducing agent. If desired, however, the peroxide intermediate of formula II-c can be separated from the reaction mixture obtained upon treatment of a compound of formula III with an oxidizing agent by any of the usual techniques, e.g., chromatographic separation, fractional crystallization, etc.

The reduction of the peroxide is conveniently carried out by employing any reducing agent conventionally used for the reduction of peroxides such as sodium sulfite, trialkylphosphite, etc. preferably in the presence of an organic solvent such as an alcohol, e.g., methanol, ethanol, etc.; dimethylformamide and the like, or when using a salt of the peroxide, the reduction can be carried out in an aqueous solvent, e.g., in an aqueous alcoholic solvent. The reduction is suitably carried out at room temperature or above, preferably at a temperature between about 20°C. and 100°C.

As noted above, the hydroxyl proton of a compound of formula II can undergo a prototropic shift to form the corresponding isomeric end product of formula I. In solution the product obtained upon oxidation and reduction of an intermediate of formula III will ordinarily be a mixture of the tautomeric forms I and II. The relative amounts of the isomeric forms present is dependent upon such factors as the solvent system employed, the pH of the medium and the particular product, i.e., the meaning of B, $R_1$, $R_2$, $R_3$ and $R_4$ in formulas I and II. For example, in a solution of chloroform the product obtained upon oxidation and reduction of 2,3-dihydro-5-phenyl-5H-imidazo[2,1-a]isoindole contains a mixture of the isomers 2,3-dihydro-5-hydroxy-5-phenyl-5H-imidazo[2,1-a]isoindole and 2-(2-benzoylphenyl)-2-imidazoline in a ratio of about 1:1. The acid addition salts isolated in the ordinary manner from the reaction product of the oxidation and reduction of 2,3-dihydro-5-phenyl-5H-imidazo[2,1-a]isoindole are ordinarily obtained as structure I.

Compounds of formula II-d are prepared from the compounds of formula II by treating an acid addition salt, e.g., the hydrochloride, hydrobromide or the like, of a formula II compound with a lower alkanol preferably at an elevated temperature. The etherification can be suitably carried out using the lower alkanol as solvent or in the presence of an inert organic solvent such as ether and the like and preferably at a temperature between about room temperature and the reflux temperature of the reaction mixture, i.e., up to about 150°C.

The novel compounds of formula II-d as well as the intermediates of formulas II-c and III are obtained as racemates. It is intended to include in this invention all of the stereoisomeric forms whether they are obtained as racemic mixtures or as the separated optically active antipodes.

The intermediates of formulas III and II-c are also novel compounds which constitute part of this invention. Compounds of formula III are, in addition to being useful as intermediates in the preparation of compounds of formulas I and II, also useful as psychostimulant, anti-inflammatory and anti-pyretic agents.

Alternatively, the compounds of formulas III, II and I can be prepared according to the following reaction scheme:

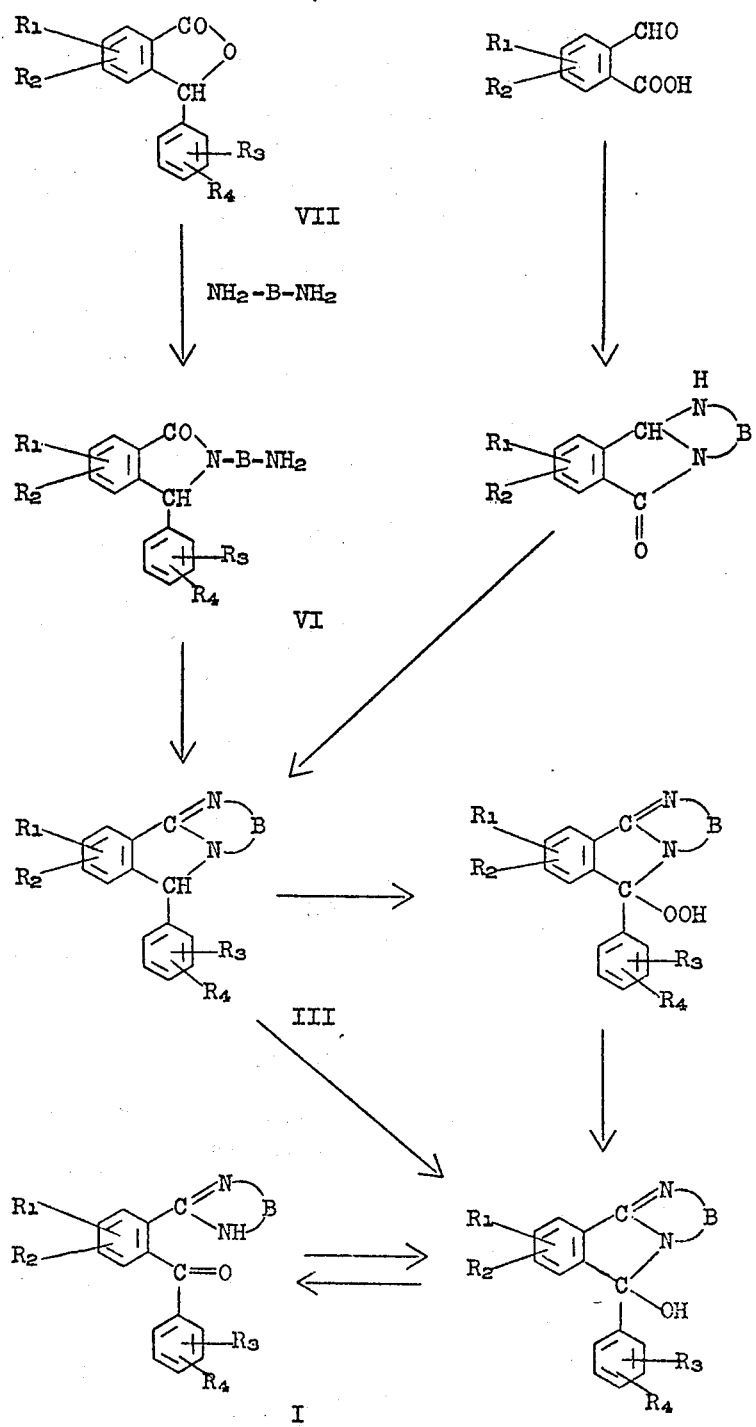

wherein $R_1$, $R_2$, $R_3$, $R_4$ and B each have the same meaning as hereinabove.

According to one alternative synthesis outlined above the intermediates of formula III are prepared by cyclization of a phthalimidine of formula VI. The cyclization of a phthalimidine of formula VI to form an intermediate of formula III is readily accomplished by treatment with a Lewis acid such as titanium chloride, boron trifluoride and the like. The oxidation and reduction of the formula II intermediates to form the desired end products is accomplished by the procedures described above.

The reaction with Lewis acid is preferably carried out in the presence of an inert organic solvent, e.g., hydrocarbon solvents such as toluene, xylene and the like, and preferably at an elevated temperature suitably at the reflux temperature of the solvent employed. A preferred temperature range for the cyclization of the phthalimidines is a temperature between about 50°C to about 200°C. The phthalimidine intermediates of formula VI are prepared by condensing a 3-phenylphthalide of formula VII with a diamine of formula XII. The 3-phenylphthalides of formula VII and the diamines of formula X employed as starting materials are known compounds or analogs of known compounds which are readily accessible in analogy to the known compounds.

The preparation of the formula VI intermediates is catalyzed by salts of organic bases such as pyridine, trialkylamine, quinoline, ethylenediamine, etc., with acids such as an organic acid, a mineral acid, e.g., sulfuric acid, hydrohalic acid, phosphoric acid, perchloric acid, etc., or a Lewis acid such as zinc chloride, aluminum chloride, etc. Preferred catalysts for the reaction are the salts of ethylenediamine and pyridine such as pyridinium hydrochloride and the like. It is preferred to carry out the reaction with an excess of the ethylenediamine reactant as solvent. However, inert organic solvents such as alcohols, e.g., methanol, ethanol, etc.; hydrocarbons, e.g., benzene, toluene, etc.; ethers, e.g., tetrahydrofuran, dioxane, etc., can also be employed. The reaction is carried out at an elevated temperature, preferably at a temperature about 100°C. Especially suitable temperatures for carrying out this reaction are temperatures between about 180°C. and about 250°C.

The preparation of the phthalimidines of formula VI does not itself constitute part of this invention and is given here for the sake of completeness only.

Alternatively, the intermediates of formula III can be prepared from the corresponding diazacycloalkenylisoindolones of formula VIII by reaction with an appropriate phenyl-organometallic derivative of the formula

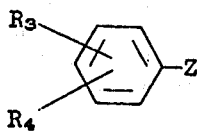
XI wherein $R_3$ and $R_4$ each have the same meaning as hereinabove; and Z is Li, MgBr, MgI, MgCl or the like.

The reaction with a phenyl-lithium derivative of formula XI can be conveniently carried out in the presence of an inert solvent at about room temperature. Higher or lower temperatures suitably in the range of about 10°C. to about 100°C. can also be employed. Suitable solvents that can be utilized are, for example, the hydrocarbons such as benzene, toluene, xylene, etc., ethers, and the like or mixtures of each solvents.

The diazacycloalkenylisoindolone intermediates of formula VIII are also novel compounds and thus constitute a part of this invention. They are readily prepared by the condensation of a phthalaldehydic acid derivative of formula IX with an alkylene diamine of formula XII. The condensation reaction is conveniently carried out in the presence of an inert organic solvent and preferably at an elevated temperature. Suitable temperatures for carrying out the condensation reaction are temperatures between about 20°C. and about 100°C. or the boiling point of the reaction mixture. As solvent for the condensation there can be suitably employed any of the usual organic solvents such as alcohols, hydrocarbons, ethers, etc.

The phthalaldehydic acid derivatives of formula IX are known starting materials or analogs of known compounds readily obtained by known processes.

In still another alternative process, the end products of formula I can be obtained by oxidation of a 1-phenyl-2-aminoalkylisoindoline derivative as outlined below:

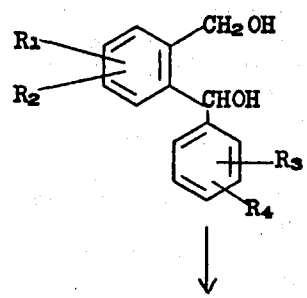
V

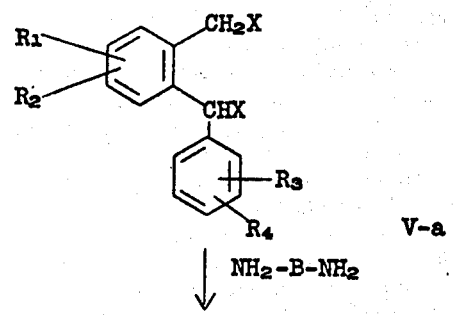
V-a

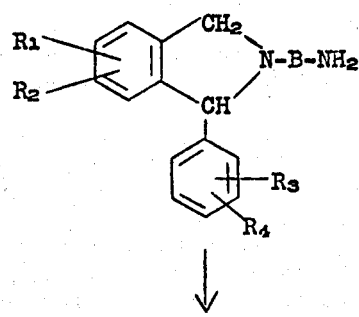
VI

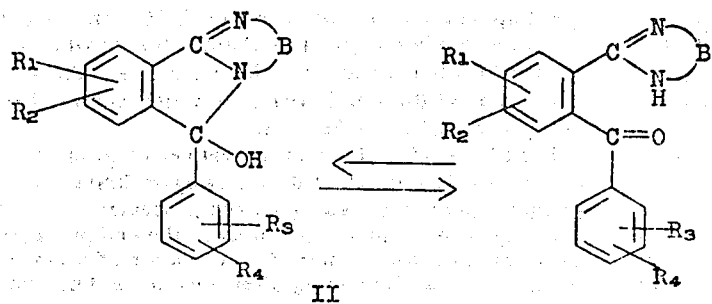

wherein B, $R_1$, $R_2$, $R_3$ and $R_4$ are as defined hereinabove; and X is halogen, preferably chlorine, iodine or bromine or other similar leaving groups such as mesyloxy, tosyloxy and the like.

The oxidation is accomplished by treating with an oxidizing agent such as gaseous oxygen or chemical oxidants such as chromium trioxide in acetic acid and the like.

The reaction is preferably carried out in the presence of an organic solvent such as, for example, hydrocarbon solvents, e.g., benzene, toluene or the like; alkanoic acids, e.g., acetic acid, propionic acid, etc.; ethers, alcohols and solvents such as dimethylformamide, etc. The reaction can be suitably accomplished at room temperature or at an elevated temperature, preferably at a temperature between about 20°C. and 100°C. The 1-phenyl-2-aminoalkylisoindoline intermediates are prepared from the diols of formula V via a diester of formula V-a. The diesters are obtained by the usual techniques for esterification, e.g., treating the diol with one of the ordinary esterifying agents such as a halo acid and halides such as phosphorous halide, thionyl halide, tosyl halide, etc. The diester of formula V-a is in turn converted to the 1-phenyl-2-aminoalkylisoindoline intermediate of formula VI by condensing with a diamine of formula XII.

The reaction with diamine is conveniently carried out by adding the diester of formula V-a to the diamine at room temperature. Preferably, there is employed a large molar excess of diamine. The reaction can also be carried out at temperatures above or below room temperature, although for practical reasons it is preferred to operate at a temperature between about 0°C. and 100°C. The reaction is suitably carried out in the presence of an organic solvent such as, for example, benzene, methylene chloride, ether, tetrahydrofuran and the like; or, in the case where either or both of the reactants are liquid under the conditions employed in the reaction, the reaction is conveniently carried out in the absence of a solvent.

The preparation of the 1-phenyl-2-aminoalkylisoindolines of formula VI does not constitute part of this invention and is given here for the sake of completeness only.

As used throughout this application the term "lower alkyl" denotes straight and branched chain hydrocarbons containing 1 to 6 carbon atoms such as methyl, ethyl, propyl, isopropyl, butyl, sec.-butyl, t.-butyl and the like. The term "lower alkoxy" denotes lower alkylether groups wherein the alkyl group is as defined above. The term "halogen" as used herein includes all four halogens, i.e., chlorine, bromine, iodine and fluorine.

Suitable salts of the compounds of formula I are prepared from nontoxic organic and inorganic acids. Suitable organic acids are, for example, maleic acid, fumaric acid, ascorbic acid, tartaric acid, salicylic acid, succinic acid, citric acid and the like. Suitable inorganic acids are, for example, the hydrohalic acids, e.g., hydrochloric acid and hydrobromic acid; sulfuric acid, sulfamic acid, phosphoric acid, etc. The acid addition salts are readily prepared by the usual techniques for the preparation of acid addition salts which are readily apparent to those skilled in the art.

As has been indicated hereinabove the novel end products of this invention, i.e., the compounds of the formula I and their pharmaceutically acceptable acid addition salts and the compounds of formula II-d and their pharmaceutically acceptable acid addition salts, are useful as psychostimulants. When administered, for example, orally, to animals such as mice they produce a direct-acting stimulant effect of long duration in single doses in amounts ranging from 0.03 mg/kg to 50 mg/kg. By way of illustration the compound of Example 10, 2-(2-benzoylphenyl)-2-imidazoline, which has an $LD_{50}$ in mice of 200 mg/kg p.o.; 130 mg/kg s.c.; 77 mg/kg i.p.; and 37 mg/kg i.v. (Proc. Soc. Exptl. Biol. Med., Vol. 57, page 261); reversed the hypothermia induced by reserpine in mice at a dose of 10 mg/kg s.c. (Med. Pharmacol. Exp., Vol. 12, pages 226–232, 1965); prevented the ptosis induced by tetrabenazene in mice at .06 mg/kg p.o. (Pletscher et al., Progress. Drug Research, Vol. II, page 417, 1960 ); reversed the reserpine (10 mg/kg s.c.) induced sedation in mice by increasing their locomotor activity at doses of 25–50 mg/kg p.o. (Med. Pharmacol. Exp., Vol. 12, pages 226–232, 1965); and potentiated the effects of β-(3,4-dihydroxyphenyl)-α-alanine (DOPA) in mice at a dose of 6.25 mg/kg i.p. (Arc. Exp. Path. and Pharm., Vol. 140, page 237). The compounds of this invention have psychostimulant effects qualitatively similar in many respects to those of imipramine and amphetamine which are well known for their therapeutic uses and properties. Among other illustrative compounds of formulas I and II-d which have been similarly tested and found to be qualitatively similar to 2-(2-benzoylphenyl)-2-imidazoline, there can be named by way of exemplification the following:

5-(4-chlorophenyl)-2,3-dihydro-5-hydroxy-5H-imidazo[2,1-a]isoindole;

2,3-dihydro-5-hydroxy-5-(4-methoxyphenyl)-5H-imidazo[2,1-a]-isoindole; and 2,3-dihydro-5-methoxy-5-phenyl-5H-imidazo[2,1-a]isoindole.

The activity of the claimed compounds of formulas I and II-d first demonstrated by pharmacological evaluation in warm-blooded animals as indicated herein permits their use in therapy in the same general manner as imipramine or amphetamine, which latter compounds exhibit psychostimulant activity in the DOPA potentiation test at doses of 10 mg/kg i.p. and 1.0 mg/kg i.p. respectively and in the ptosis prevention test at doses of >60 mg/kg and 7.5 mg/kg respectively. As a further illustration of the psychostimulant activity of the compounds of formulas I and II-d, the compound of Example 21, 2,3,4,5-tetrahydro-7-hydroxy-7-phenyl-7H-diazepino[2,1-a]isoindole, which has an $LD_{50}$ of 40 mg/kg i.v., prevented the ptosis induced by tetrabenazene at 0.4 mg/kg p.o.; reversed the hypothermia and hypometabolic effects induced by reserpine (10 mg/kg s.c.) in mice at 25 mg/kg p.o.; and potentiated the effects of DOPA in mice at a dose of 7.5 mg/kg i.p. The compounds of this invention thus demonstrate a pattern of activity associated with anti-depressants of known clinical efficacy and are similarly useful as psychostimulants in the treatment of depressed states, for example, in cases of simple depression or in cases of chronic nervous exhaustion.

In addition to their use as psychostimulants, the compounds of formulas I and II-d are also useful as analgesic agents. By way of example, 2-(2-benzoylphenyl)-2-imidazoline, when submitted to standard pharmacological tests for analgesic properties, exhibited marked activity in the writhing test in mice at doses of 30.8 mg/kg p.o. and 5 mg/kg s.c. and anti-pyretic activity in rats at doses of 6.25 to 50 mg/kg p.o. The compound also showed potent anti-inflammatory activity in the inflamed rat foot test at 6.25 mg/kg p.o. and anti-edema activity in the Carrageenan anti-edema rat paw test at 6.25 mg/kg p.o. In the unanesthetized cat test for muscle relaxants the compound was active at a dose of 2.5 mg/kg p.o. Based on the foregoing pharmacological tests in animals, the analgesic properties of the novel end products of this invention and particularly those of 2-(2-benzoylphenyl)-2-imidazoline can be likened to the analgesic properties of phenylbutazone which is well known for its therapeutic uses and properties. Compounds of formulas I and II-d are also useful as anorexigenic agents owing to their marked activity in the 4-hour anti-obesity test in rats wherein compounds of this class have demonstrated activity qualitatively similar to amphetamine. Compounds of this series have also demonstrated useful cardiovascular properties. For example, 2-(2-benzoylphenyl)-2-imidazoline in dogs at 4 mg/kg i.v. produced an increase in blood pressure of 10 mm. Hg after 2 minutes followed by gradual increase to 25 mm. Hg.

Compounds of formula I have also been found to be active as anti-fungal agents. For example, they have been found to be active in vitro in *Candida albicans*, *Microsporum audouini* and *Trichophyton mentagrophytes*. Accordingly, these compounds can be employed as anti-fungal agents in the treatment of pathogenic diseases caused by these organisms. They can, for example, be employed in the treatment of infectious fungal diseases such as moniliasis and dermatomycoses. For the treatment of fungal infections the compounds of formula I can be employed by applying a suitable composition containing about 0.1 mg. to about 5 g. of active material over the site of the infection. Suitable compositions are prepared by embodying a compound of formula I or a pharmaceutically acceptable salt thereof in a conventional carrier suitable for topical administration.

The novel end products of this invention, i.e., the compounds of formulas I and II-d are mostly white crystalline odorless solids melting at temperatures in the order of 200°C. They have basic properties and can be conveniently prepared in the form of their acid addition salts. Suitable salts are prepared as described hereinabove. The salts are characteristically white crystalline odorless solids soluble in water and have good stability under ordinary conditions.

The compounds of formulas I and II-d, preferably in the form of their acid addition salts can be formulated into preparations suitable for administration by enteral or parenteral routes. They can be embodied in pharmaceutical unit dosage forms containing from about 0.5 mg. to about 100 mg. of active material, i.e., a compound of formulas I or II-d or a salt thereof. Parenteral formulations will ordinarily contain less of the active substance than compositions intended for enteral, e.g., oral, administration. For oral administration the products of this invention can be prepared as tablets, capsules and the like containing about 10 to 50 mg. of active material. Formulations suitable for oral administration may be such as to provide either immediate, or in the alternative, sustained release of the active drug. In general, the formulations will be prepared with pharmaceutically acceptable adjuvant materials comprising from about 60 to about 98 per cent of the weight of the compositions in oral dosage form.

For parenteral administration the compounds can be formulated with a liquid diluent, for example, distilled water, in the preparation of a suitable parenteral dosage form. The preferred parenteral dosage form will contain from about 0.5 mg. to about 15 mg. of the active drug. In general, the compounds of this invention are formulated with conventional inert adjuvants into dosage forms suitable for enteral or parenteral administration following the conventional techniques and procedures of the prior art. Suitable dosage forms include tablets and capsules as well as solutions, emulsions and suspensions. The inert adjuvants which are suitable for use in preparing the various dosage forms include liquids and solids inorganic or organic in nature such as water, gelatin, lactose, starch, magnesium stearate, talc, vegetable oils, gums polyalkylene glycols, Vaseline, etc. Additionally, the compounds can be used in combination with preservatives, stabilizers, wetting or emulsifying agents, salts for altering the osmotic pressure, buffers, etc. If desired, the compounds can be used also in admixture with other therapeutically valuable substances. Specific embodiments showing illustrative formulations of an exemplary compound of formula I follow.

| Tablet Formulation | Per Tablet |
| --- | --- |
| 2-(2-benzoylphenyl)-2-imidazoline | 10.0 mg. |
| Lactose | 113.5 mg. |
| Corn Starch | 70.5 mg. |
| Pregelatinized Corn Starch | 8.0 mg. |
| Calcium Stearate | 3.0 mg. |
| Total Weight | 205.0 mg. |

Procedure:
1. 2-(2-Benzoylphenyl)-2-imidazoline was mixed with the lactose, corn starch, and pregelatinized corn starch in a suitable size mixer.
2. The mix was passed through a Fitzpatrick Comminuting Machine fitted with a No. 1A screen and with knives forward.
3. The mix was returned to the mixer and moistened with water to a thick paste. The moist mass was passed through a No. 12 screen and the moist granules were dried on paper-lined trays at 100°F.
4. The dried granules were returned to the mixer, the calcium stearate was added and mixed well.
5. The granules were compressed at a tablet weight of 200 mg., using standard concave punches having a diameter of 5/16 inch.

| Suppository Formulation | Per 1.3 Gram Suppository |
| --- | --- |
| 2-(2-benzoylphenyl)-2-imidazoline | 0.025 gram |
| Wecobee M (E. F. Drew Company 522 Fifth Avenue New York, New York) | 1.230 gram |
| Carnauba Wax | 0.045 gram |

Procedure:
1. The Wecobee M and the carnauba wax were melted in a suitable size glass-lined container (stainless steel may also be used), mixed well and cooled to 45°C.
2. 2-(2-Benzoylphenyl)-2-imidazoline, which had been reduced to a fine powder with no lumps, was added and stirred until completely and uniformly dispersed.
3. The mixture was poured into suppository molds to yield suppositories having an individual weight of 1.3 grams.
4. The suppositories were cooled and removed from molds. They were individually wrapped in wax paper for packaging. (Foil may also be used.)

| Capsule Formulation | Per Capsule |
| --- | --- |
| 2-(2-benzoylphenyl)-2-imidazoline | 25 mg. |
| Lactose | 158 mg. |
| Corn Starch | 37 mg. |
| Talc | 5 mg. |
| Total Weight | 255 mg. |

Procedure:
1. 2-(2-Benzoylphenyl)-2-imidazoline was mixed with the lactose and corn starch in a suitable mixer.
2. The mixture was further blended by passing through a Fitzpatrick Comminuting Machine with a No. 1A screen with knives forward.
3. The blended powder was returned to the mixer, the talc added and blended thoroughly. The mixture was then filled into No. 4 hard shell gelatin capsules on a Parke Davis capsulating machine (any similar type machine may be used).

| Parenteral Formulation | Per cc. |
| --- | --- |
| 2-(2-benzoylphenyl)-2-imidazoline | 2.5 mg. |
| Tartaric Acid   q.s. ad pH 3.0 | |
| Phenol Anhydrous | 4.5 mg. |
| Water for Injection, U.S.P.   q.s. ad | 1.0 cc. |

Procedure:
1. 2-(2-Benzoylphenyl)-2-imidazoline was slurried in part of the water for injection.
2. 2-(2-Benzoylphenyl)-2-imidazoline was solubilized by slowly adding the tartaric acid to a pH of approximately 3.0.
3. The phenol anhydrous was then added.
4. The solution was filtered and allowed to stand for 24 hours. It was then filtered through an 02 Selas candle.
5. The solution was filled into desired size ampuls and sealed under an atmosphere of nitrogen.
6. All ampuls were inspected; those containing excessive amounts of fibers were rejected.

The drug was prepared in duplex ampuls, one containing the dry drug and the other containing the special diluent.

| | Dry Fill Ampul 5 cc. |
| --- | --- |
| 2-(2-benzoylphenyl)-2-imidazoline | 25 mg. |

A parenteral grade of the drug, fiber-free, was filled into the ampul using a Diehl Mater electric filler or other suitable type filler. The ampuls were sealed and sterilized at 255°F. for 2 hours.

Immediately before use the powder was solubilized with the following solution:

| | Special Diluent 2 cc. per ml. |
| --- | --- |
| Tartaric acid | 16 mg. |
| Water for Injection   q.s. to | 1.0 ml. |

In a suitable container under an atmosphere of nitrogen the tartaric acid was dissolved in part of the water for injection. The solution was made to volume, filtered through an 02 Selas candle filter and filled into 2 cc. flint ampuls. The filling should be done under an atmosphere of nitrogen. The ampuls were sealed and sterilized at 212°F. for 30 minutes. The ampuls were then inspected and those that leaked or contained fibers were discarded.

The drug in the preferred oral dosage form, i.e., tablets or capsules containing 10 to 25 mg. of active material, will be administered under ordinary circumstances three or four times daily. The parenteral composition will be administered ordinarily one or two times daily. Effective dosages for the administration of compounds of this invention, i.e., the compounds of formulas I and II-d, will, of course, depend in all instances upon the severity and individual characteristics of each case as determined by the prescribing practitioner. It will be

EXAMPLE 1

Preparation of 2-benzoylbenzaldehyde

A mixture of 1 g. of selenium dioxide and 1 g. of 2-hydroxymethylbenzhydrol in 5 ml. of acetic acid was refluxed for 4½ hours. The solution was cooled, filtered from selenium and the filtrate was poured into ice water and made alkaline with sodium hydroxide. Extraction with ether gave a yellow oil to which petroleum ether was added. White prisms were obtained which melted at 64°–67°. Ultraviolet maximum (2-propanol) at 226/7 mμ (ε = 15,750) and 251/2 mμ (ε = 18,500), inflexion at 294 mμ (ε = 2600); infrared absorption (CHCl$_3$) at 1665 cm$^{-1}$ and 1705 cm$^{-1}$ Anal. Calcd. for $C_{14}H_{10}O_2$: C, 79.98; H, 4.79; Found: C, 80.00; H, 4.68

EXAMPLE 2

Preparation of 2-(p-chlorobenzoyl)-benzaldehyde

A solution of 18.6 g. of 4'-chloro-2-hydroxymethylbenzhydrol in 100 ml. of acetic acid and 10.4 g. selenium dioxide was refluxed for 2 hours. The mixture was poured on ice and made alkaline and extracted with ether. Concentration of the ether solution and addition of petroleum ether gave pale yellow prisms which after recrystallization from a mixture of ether and petroleum ether gave 2-(p-chlorobenzoyl)-benzaldehyde melting at 112°–113°. Ultraviolet inflexion (2-propanol) at 225 mμ (ε = 17,500) and maximum at 259 mμ (ε = 22,500), infrared absorption (CHCl$_3$) at 1670 cm$^{-1}$ and 1705 cm$^{-1}$.

Anal. Calcd. for $C_{14}H_9ClO_2$: C, 68.72; H, 3.71; Found: C, 69.12; H, 3.50

EXAMPLE 3

Preparation of 2-(p-anisoyl)-benzaldehyde

A solution of 26 g. of 4'-methoxy-2-hydroxymethylbenzhydrol in 140 ml. of acetic acid and 14.5 g. selenium dioxide was refluxed for 2 hours. The mixture was filtered and the filtrate was made basic. An oil separated which crystallized on standing and was collected. Recrystallization from a mixture of methylene chloride and petroleum ether gave off-white platelets melting at 90°–91°. Ultraviolet maxima (2-propanol) at 221 mμ (ε = 21,600), 258 mμ (ε = 12,400) and 292 mμ (ε = 17,000); infrared absorption (CHCl$_3$) at 1660 cm$^{-1}$ and at 1700 cm$^{-1}$.

Anal. Calcd. for $C_{15}H_{12}O_3$: C, 74.99; H, 5.03; Found: C, 75.27; H, 5.26

EXAMPLE 4

Preparation of 2-benzoyl-4-chlorobenzaldehyde

A solution of 9.3 g. of 5-chloro-2-hydroxymethylbenzhydrol in 50 ml. of acetic acid and 5.2 g. of selenium dioxide was refluxed for 3 hours. The mixture was filtered, cooled, poured on ice, made alkaline and extracted with ether. Concentration and addition of petroleum ether gave the product as prisms which after recrystallization from a mixture of ether and petroleum ether melted at 82°–84°. Ultraviolet maxima (2-propanol) at 230 mμ (ε = 19,500) and 257 mμ (ε = 23,500); infrared absorption (CHCl$_3$) at 1675 cm$^{-1}$ and 1705 cm$^{-1}$.

Anal. Calcd. for $C_{14}H_9ClO_2$: C, 68.72; H, 3.71 Found: C, 69.05; H, 3.87

EXAMPLE 5

Preparation of 2-(4-bromobenzoyl)-benzaldehyde

To a stirred solution of 8.2 g. of lithium aluminum hydride in 180 ml. of tetrahydrofuran was added 40 g. of 2-(4-bromobenzoyl)benzoic acid in the course of 30 minutes. The mixture, after being kept at 25° for 2 hours, was cooled and 40 ml. of a saturated sodium sulfate solution was added slowly. The mixture was filtered and the filtrate concentrated. The resulting oily residue was dissolved in 32 ml. of acetic acid and 96 ml. of xylene. This solution was added to a mixture of 17.1 g. of selenium dioxide in 60 ml. of acetic acid and 120 ml. of xylene and refluxed for 17 hours. During this time about 22 ml. of an aqueous phase had collected in a Dean Stark receiver. The solution was filtered, washed with sodium hydroxide and concentrated. Addition of petroleum ether gave white prisms melting at 103°–109°. Recrystallization from a mixture of ether and petroleum ether raised the melting point to 110°–113°. Ultraviolet inflexion (2-propanol) at 225 mμ (ε = 17,500) and maximum at 261 mμ (ε = 22,200); infrared absorption (CHCl$_3$) at 1675 cm$^{-1}$ and 1705 cm$^{-1}$.

Anal. Calcd. for $C_{14}H_9BrO_2$: C, 58.16; H, 3.14; Found: C, 57.86; H, 3.41

EXAMPLE 6

Preparation of 2,3-dihydro-5-phenyl-5H-imidazo[2,1-a]isoindole sulfate from 2-benzoylbenzaldehyde A solution of 21 g. of o-benzoylbenzaldehyde in 250 ml. of toluene and 34 ml. of ethylenediamine was refluxed for 24 hours. During this time 11.5 ml. of an aqueous phase was separated in a Dean Stark receiver. The reaction mixture was concentrated in vacuo to an orange oil which was dissolved in ethyl acetate and washed twice with water. The solution was dried and concentrated, dissolved in 200 ml. of ethyl acetate and a solution of 5.3 ml. of concentrated sulfuric acid in 100 ml. of ethanol was added. A crystalline precipitate was collected which after recrystallization from a mixture of methanol and ethyl acetate gave white prisms melting at 226°–229° dec. Ultraviolet maxima (2-propanol) at 240 mμ (ε = 15,000) and 276 mμ (ε = 5,400); infrared absorption (KBr) 1660 cm$^{-1}$.

Anal. Calcd. for $C_{16}H_{14}N_2 \cdot H_2SO_4$: C, 57.82; H, 4.85; N, 8.43; Found: C, 57.61; H, 4.81; N, 8.73

The hydrochloride of 2,3-dihydro-5-phenyl-5H-imidazo[2,1-a]isoindole was prepared from the corresponding base with aqueous 1 N hydrochloric acid. On recrystallization from a mixture of methanol and toluene, white prisms melting at 226°–228° dec. were obtained. Nmr peaks (DMSO) at δ 3.6–4.6 (4H, multiplet), at δ 6.13 (1H, singlet), at δ 7.3–7.9 (9H, multiplet).

EXAMPLE 7

Preparation of
2,3-dihydro-5-phenyl-5H-imidazo[2,1-a]isoindole sulfate from 2-(2-aminoethyl)-3-phenylphthalimidine A solution of 1.2 ml. of titanium tetrachloride in 30 ml. of xylene was added at 25° to a stirred solution of 2.5 g. of 2-(2-aminoethyl)-3-phenylphthalimidine in 150 ml. of xylene. The mixture was refluxed for 18 hours, cooled and washed with an aqueous solution of sodium carbonate. The xylene solution was extracted with 2N hydrochloric acid. The acidic extract was poured on ice and made alkaline with sodium hydroxide. The solution was extracted with ethyl acetate and the extract was concentrated. Addition of a solution of sulfuric acid in a mixture of ethanol and tetrahydrofuran and further dilution with ethyl acetate gave a crystalline precipitate. Recrystallization from a mixture of methanol and ethyl acetate gave the product as white prisms melting at 225°–228° dec.

EXAMPLE 8

Preparation of
2,3-dihydro-5-hydroperoxy-5-phenyl-5H-imidazo[2,1-a]isoindole

The base liberated from 16.6 g. of 2,3-dihydro-5-phenyl-5H-imidazo[2,1-a]isoindole sulfate was dissolved in 50 ml. of ethanol and 11 ml. of a 30 percent by weight aqueous solution of hydrogen peroxide was added. The mixture was stirred at 25° for 40 hours. A crystalline crop was collected and placed on a column containing 250 g. of silica gel. Elution with a mixture of 1 part of methanol (volume) and 1 part of chloroform (volume) gave fractions from which on concentration a crystalline residue was obtained. Recrystallization from a mixture of methanol and chloroform gave the product as white prisms melting at 167°–168° dec. Ultraviolet inflexions (2-propanol) at 232 mμ (ε = 14,000) and 290 mμ (ε = 2600), maxima at 269 mμ (ε = 4000) and 275 mμ (ε = 4400), infrared absorption (KBr) at 1665 cm$^{-1}$.

Anal. Calcd. for $C_{16}H_{14}N_2O_2$: C, 72.16; H, 5.30; N, 10.52; Found: C, 72.09; H, 5.39; N, 10.22

The hydrochloride of 2,3-dihydro-5-hydroperoxy-5-phenyl-5H-imidazo[2,1-a]isoindole was prepared with methanolic hydrogen chloride and after recrystallization from a mixture of methanol and ether gave white platelets melting at 158°–159° dec. Ultraviolet maxima (2-propanol) at 245 mμ (ε = 14,800) and 278 mμ (ε = 5200); infrared absorption (KBr) at 1680 cm$^{-1}$.

Anal. Calcd. for $C_{16}H_{14}N_2O_2$·HCl: C, 63.47; H, 4.99; Cl, 11.71; Found: C, 63.63; H, 4.83; Cl, 11.79

EXAMPLE 9

Preparation of
5-(p-chlorophenyl)-2,3-dihydro-5-hydroperoxy-5H-imidazo[2,1-a]isoindole hydrochloride 1 Gram of 2-(p-chlorobenzoyl)-benzaldehyde was thoroughly mixed with 0.9 g. of ethylenediamine toluene sulfonate and heated in a metal bath (bath temperature, 120°–125°) for 1 minute. On cooling a deep yellow glassy material was obtained which on addition of methylene chloride, ethyl acetate and petroleum ether gave a crystalline precipitate which was treated with ice cold aqueous sodium hydroxide. The mixture was extracted with ether and the extract was exposed to air at 25° for 18 hours. A crystalline crop was collected and suspended in methylene chloride. Addition of ethereal hydrogen chloride gave a crystalline material which after recrystallization from a mixture of methanol and ether gave white prisms melting at 175°–177° dec. Ultraviolet inflexion (2-propanol) at 223 mμ (ε = 21,800) and 279 mμ (ε = 5600), maximum at 243 mμ (ε = 15,500); infrared absorption (KBr) at 1670 cm$^{-1}$.

Anal. Calcd. for $C_{16}H_{13}ClN_2O_2$·HCl: C, 56.99; H, 4.18; Cl, 21.03; N, 8.31; Found: C, 57.14; H, 4.15; Cl, 21.02; N, 8.30

EXAMPLE 10

Preparation of 2-(2-benzoylphenyl)-2-imidazoline from 2,3-dihydro5-phenyl-5H-imidazo[2,1-a]isoindole To a suspension of 8.5 g. of 2,3-dihydro-5-phenyl-5H-imidazo[2,1-a]isoindole sulfate in water was added 50 ml. of 1N aqueous sodium hydroxide. Extraction with methylene chloride and concentration gave an orange oil which was dissolved in a mixture of 30 ml. of methylene chloride and 30 ml. of ethanol. To this solution was added 2.3 ml. of 30 percent by weight hydrogen peroxide. After stirring at 25° for 18 hours, a precipitate was collected which after recrystallization from methanol gave white prisms melting at 194°–196° dec. Ultraviolet inflexions (2-propanol) at 225 mμ (ε = 15,500) and 290 mμ (ε = 2250), maxima at 269 mμ (ε = 4100) and 276 mμ (ε = 4250); infrared absorption (KBr) 1660 cm$^{-1}$.

Anal. Calcd. for $C_{16}H_{14}N_2O$: C, 76.78; H, 5.64; N, 11.19; Found: C, 76.42; H, 5.79; N, 11.13

The 2-(2-benzoylphenyl)-2-imidazoline prepared in this manner can form the isomeric 2,3-dihydro-5-hydroxy-5-phenyl-5H-imidazo[2,1-a]isoindole.

The hydrochloride was prepared by adding a solution of hydrogen chloride in methanol to a suspension of 2-(2-benzoylphenyl)-2-imidazoline in methanol. Ether was added and the crystalline precipitate was collected. Recrystallization from a mixture of methanol and ether gave white prisms melting at 173°–176° dec. Ultraviolet maximum (2-propanol) at 252 mμ (ε = 13,600); infrared absorption (KBr) at 1665 cm$^{-1}$.

Anal. Calcd. for $C_{16}H_{14}N_2O$·HCl: Cl, 12.36; Found: Cl, 12.22

The hydrobromide was prepared by adding an aqueous solution of hydrobromic acid to a suspension of 2-(2-benzoylphenyl)-2-imidazoline in ethanol. Addition of ether gave a precipitate which after recrystallization from a mixture of ethanol and ether gave white platelets melting at 193°–194° dec.

Anal. Calcd. for $C_{16}H_{14}N_2O$·HBr: Br, 24.13; Found: Br, 24.15

EXAMPLE 11

Preparation of 2-(2-benzoylphenyl)-2-imidazoline from
2,3-dihydro-5-hydroperoxy-5-phenyl-5H-imidazo[2,1-a]isoindole A solution of 0.7 g. of sodium sulfite heptahydrate in 3 ml. of water was added to 0.5 g. of 2,3-dihydro-5-hydroperoxy-5-phenyl-5H-imidazo[2,1-a]isoindole in 7 ml. of dimethylformamide. The solution was heated to 100° for 15 minutes. On cooling and addition of 20 ml. of water, 2-(2-benzoylphenyl)-2-imidazoline was obtained.

EXAMPLE 12

Preparation of 2-(2-benzoylphenyl)-2-imidazoline from 2,3-dihydro-5-hydroperoxy-5-phenyl-5H-imidazo[2,1-a]isoindole A solution of 0.1 g. of 2,3-dihydro-5-hydroperoxy-5-phenyl-5H-imidazo[2,1-a]isoindole and 0.33 g. of triethylphosphite in 20 ml. of ethanol was kept on a steam bath for 5 minutes, then 18 hours at 25°. The solution was concentrated in vacuo and on addition of water 2-(2-benzoylphenyl)-2-imidazoline was obtained.

EXAMPLE 13

Preparation of 2-(2-benzoylphenyl)-2-imidazoline from 2-(2-aminoethyl)-1-phenylisoindoline A solution of 3.3 g. of chromium trioxide and 5.9 g. of 2-(2-aminoethyl)-1-phenylisoindoline in 250 ml. of acetic acid was stirred at 55°–60° for 18 hours. The solution was cooled, poured on ice and made alkaline. Extraction with methylene chloride and removal of the solvent gave a brown oil which partly crystallized. Recrystallization from a mixture of chloroform and ethyl acetate gave the product as white prisms melting at 194°–196° dec.

EXAMPLE 14

Preparation of 2-(2-aminoethyl)-1-phenylisoindoline

A solution of 127 g. (0.59 mole) of 2-hydroxymethylbenzhydrol was dissolved in 900 ml. of benzene, 80 g. of anhydrous magnesium sulfate was added and the mixture was cooled in an ice bath. Hydrogen bromide was bubbled into the stirred solution until saturation which took about 30 minutes. During this time the temperature of the solution was kept at 15°–18°. The ice bath was removed and the temperature was allowed to rise to 35° in the course of 1 hour. The mixture was heated for another hour at 40°–45° on a steam bath. During the whole time hydrogen bromide was passed into the solution to keep it saturated. The mixture was filtered and the solution was concentrated in vacuo to give a red oil which was dissolved in 200 ml. of benzene and added to 342 g. (5.7 moles) of ethylenediamine in the course of 15 minutes. During the addition the mixture was stirred and cooled to maintain a temperature of ca. 40°. The mixture was stirred at 25° for 70 minutes. Two layers were obtained and separated. The benzene layer was washed with water and concentrated in vacuo. The residual oil was dissolved in 250 ml. of ether. This solution was extracted twice with 300 ml. of cold 1N hydrochloric acid. The acidic aqueous phase was made alkaline with aqueous sodium hydroxide and extracted with 350 ml. of ether. The ethereal solution was washed with 250 ml. of water, dried and concentrated. The residue was an amber oil which crystallized on scratching. This material melted up to ca. 45°.

By analogy there were also prepared the following:
2-(3-aminopropyl)-1-phenylisoindoline
2-(2-aminoethyl)-6-chloro-1-phenylisoindoline
2-(2-aminoethyl)-1-(p-methoxyphenyl)isoindoline
2-(4-aminobutyl)-1-phenylisoindoline
2-(2-amino-2-methylpropyl)-1-phenylisoindoline
2-(2-aminopropyl)-1-phenylisoindoline 2-(2-aminoethyl)-1-(p-hydroxyphenyl)isoindoline.

EXAMPLE 15

Preparation of 2-[2'-(4-chlorobenzoyl)phenyl]-2-imidazoline

To 1 ml. of ethylenediamine was added 1 g. of 2-(p-chlorobenzoyl)-benzaldehyde in small portions. An exothermic reaction took place and after 5 minutes the reaction mixture was poured into ice water. A yellow solid precipitate was collected and dissolved in methylene chloride. Ether and petroleum ether were added and the solution was shaken in air at 25°. A crystalline precipitate was obtained which after recrystallization from a mixture of methylene chloride and methanol gave white needles melting at 178°–180° dec. Ultraviolet maxima (2-propanol) at 223 m$\mu$ ($\epsilon = 21,250$), 268 m$\mu$ ($\epsilon = 4300$), 275 m$\mu$ ($\epsilon = 4320$), inflexion at 290 m$\mu$ ($\epsilon = 2200$); infrared absorption (KBr) at 1660 cm$^{-1}$.

Anal. Calcd. for $C_{16}H_{13}ClN_2O$: C, 67.49; H, 4.60; Found: C, 67.38; H, 4.56

The 2-[2'-(4-chlorobenzoyl)phenyl]-2-imidazoline prepared in this manner can form the isomeric 5-(4-chlorophenyl)-2,3-dihydro-5-hydroxy-5H-imidazo[2,1-a]isoindole.

The hydrochloride was prepared by adding a solution of hydrogen chloride in ether to a suspension of 5-(4-chlorophenyl)-2,3-dihydro-5-hydroxy-5H-imidazo[2,1-a]isoindole. After stirring for 30 minutes a crystalline crop was collected and recrystallized from a mixture of chloroform and ether to give white prisms melting at 168°–171° dec. Ultraviolet inflexion (2-propanol) at 220 m$\mu$ ($\epsilon = 22,000$), maxima at 252 m$\mu$ ($\epsilon = 12,900$), 266 m$\mu$ ($\epsilon = 13,000$); infrared absorption (KBr) at 1670 cm$^{-1}$.

Anal. Calcd. for $C_{16}H_{13}ClN_2O \cdot HCl$: Cl, 22.08; Found: Cl, 22.18

EXAMPLE 16

Preparation of 2-[2'-(4-anisoyl)phenyl]-2-imidazoline

To 4 ml. of ethylenediamine was added 2 g. of 2-(p-anisoyl)benzaldehyde in small portions. The solution was stirred for 10 minutes, poured into ice water and extracted with methylene chloride. The methylene chloride solution was concentrated, the residue was dissolved in ethanol and a stream of air was passed through the solution for 18 hours. A crystalline precipitate was collected and after recrystallization from a mixture of chloroform and ether gave white prisms melting at 171°–174° dec. Ultraviolet maxima (2-propanol) at 227 m$\mu$ ($\epsilon = 20,200$), 277 m$\mu$ ($\epsilon = 8800$), 282 m$\mu$ ($\epsilon = 8750$), inflexion at 292 m$\mu$ ($\epsilon = 7200$); infrared absorption (KBr) at 1660 cm$^{-1}$.

Anal. Calcd. for $C_{17}H_{16}N_2O_2$: C, 72.84; H, 5.75; N, 9.99; Found: C, 73.07; H, 5.71; N, 9.83

The 2-[2'-(4-anisoyl)phenyl]-2-imidazoline prepared in this manner can form the isomeric 2,3-dihydro-5-hydroxy-5-(4-methoxyphenyl)-5H-imidazo[2,1-a]isoindole.

EXAMPLE 17

Preparation of 2-[4'-chloro-2'-benzoylphenyl]-2-imidazoline

To 2 ml. of ethylenediamine was added 0.9 g. of 2-benzoyl-4-chlorobenzaldehyde in small portions. The solution was stirred for 10 minutes, poured into ice water and the solid yellow precipitate was collected. This solid was dissolved in ether and shaken in air for 45 minutes. A white precipitate was obtained which after recrystallization from a mixture of methylene chloride and methanol melted at 200°–202° dec. Ultraviolet maxima (2-propanol) at 242 m$\mu$ ($\epsilon$ = 17,500), 278 m$\mu$ ($\epsilon$ = 3800), 286 m$\mu$ ($\epsilon$ = 3300), inflexions at 270 m$\mu$ ($\epsilon$ = 3450), 295 m$\mu$ ($\epsilon$ = 2400); infrared absorption (KBr) at 1665 cm$^{-1}$.

Anal. Calcd. for $C_{16}H_{13}ClN_2O$: C, 67.49; H, 4.60; Found: C, 67.42; H, 4.90

The 2-[4'-chloro-2'-benzoylphenyl]-2-imidazoline prepared in this manner can form the isomeric 7-chloro-2,3-dihydro-5-hydroxy-5-phenyl-5H-imidazo[2,1-a]isoindole.

EXAMPLE 18

Preparation of 2-[2-(4-bromobenzoyl)phenyl]-2-imidazoline

A solution of 6 g. of 2-(4-bromobenzoyl)-benzaldehyde and 6.6 ml. of ethylenediamine in 50 ml. of toluene was refluxed for 18 hours. During this time 0.5 ml. of an aqueous phase had separated in a Dean Stark receiver. The mixture was concentrated in vacuo and the residual orange oil was dissolved in a mixture containing 15 ml. of ethanol, 15 ml. of methylene chloride and 1.5 ml. of a 30 percent by weight aqueous solution of hydrogen peroxide. After stirring at 25° for 18 hours a white precipitate was collected which after recrystallization from methanol gave white needles melting at 187°–189° dec. Ultraviolet maxima (2-propanol) at 227 m$\mu$ ($\epsilon$ = 22,800), 259 m$\mu$ ($\epsilon$ = 4700), 275 m$\mu$ ($\epsilon$ = 4800), inflexion at 292 m$\mu$ ($\epsilon$ = 2300); infrared absorption (KBr) at 1660 cm$^{-1}$.

Anal. Calcd. for $C_{16}H_{13}BrN_2O$: C, 58.37; H, 3.98; Found: C, 58.27; H, 3.75

The 2-[2-(4-bromobenzoyl)phenyl]-2-imidazoline prepared in this manner can form the isomeric 5-(4-bromophenyl)-2,3-dihydro-5-hydroxy-5H-imidazo[2,1-a]isoindole.

The hydrochloride was prepared by adding ethereal hydrogen chloride to a solution of 5-(4-bromophenyl)-2,3-dihydro-5-hydroxy-5H-imidazo[2,1-a]isoindole in a mixture of methylene chloride and methanol. The precipitate was recrystallized from a mixture of ethanol and ether to give white prisms melting at 155°–158° dec. Ultraviolet inflexion (2-propanol) at 223 m$\mu$ ($\epsilon$ = 20,000), maxima at 251 m$\mu$ ($\epsilon$ = 12,200) and 271 m$\mu$ ($\epsilon$ = 13,300); infrared absorption (KBr) at 1660 cm$^{-1}$.

Anal. Calcd. for $C_{16}H_{13}BrN_2O \cdot HCl$: Cl, 9.70; Found: Cl, 9.82

EXAMPLE 19

Preparation of 2,3-dihydro-5-methoxy-5-phenyl-5H-imidazo[2,1-a]isoindole hydrochloride A solution of 5 g. of 2-(2-benzoylphenyl)-2-imidazoline in 50 ml. of methanol was refluxed for 18 hours. The solution was concentrated in vacuo, dissolved in 20 ml. of methanol and 60 ml. of ether was added. Crystals precipitated and were identified as starting material. The mother liquor was concentrated and the residue was recrystallized from a mixture of methanol, methylene chloride and ether to give the product as white prisms melting at 139°–141° dec. Ultraviolet maxima (2-propanol) at 244 m$\mu$ ($\epsilon$ = 14,400) and 278 m$\mu$ ($\epsilon$ = 5100); infrared absorption (KBr) at 1670 cm$^{-1}$.

Anal. Calcd. for $C_{17}H_{16}N_2O \cdot HCl$: C, 67.83; H, 5.70; $OCH_3$, 10.32
Found: C, 67.84; H, 5.61; $OCH_3$, 10.44

The corresponding base was obtained as a colorless oil by liberating it from the hydrochloride obtained as above with alkali. Ultraviolet inflexions (0.1N KOH) at 230 m$\mu$ ($\epsilon$ = 14,600), 290 m$\mu$ ($\epsilon$ = 2700), maxima at 269 m$\mu$ ($\epsilon$ = 4200) and 275 m$\mu$ ($\epsilon$ = 4600).

Infrared absorption (smear) at 1660 cm$^{-1}$ and nmr peaks (CDCl$_3$) at $\delta$ = 3.12 (3H, singlet, OCH$_3$), $\delta$ = 2.6–3.5 (2H, multiplet, N-CH$_2$), $\delta$ = 4.2–4.5 (2H, multiplet, =N—CH$_2$), $\delta$ = 7.1–8.0 (9H, multiplet, aromatic CH).

EXAMPLE 20

Preparation of 2,3,4,6-tetrahydro-6-phenylpyrimido[2,1-a]isoindole sulfate

A solution of 10.5 g. of 2-benzoylbenzaldehyde and 22 ml. of propylenediamine in 125 ml. of toluene was refluxed for 18 hours. During this time 4.5 ml. of an aqueous phase had separated in a Dean Stark receiver. The solution was concentrated in vacuo and the residue was recrystallized from a mixture of ethanol and petroleum ether to give white prisms melting at 170°–172° dec. Ultraviolet maximum (2-propanol) at 238 m$\mu$ ($\epsilon$ = 18,200), inflexions at 246 m$\mu$ ($\epsilon$ = 16,000), 265 m$\mu$ ($\epsilon$ = 5600), 276 m$\mu$ ($\epsilon$ = 3400) and 285 m$\mu$ ($\epsilon$ = 2100); infrared absorption (KBr) at 1675 cm$^{-1}$.

Anal. Calcd. for $C_{17}H_{16}N_2 \cdot H_2SO_4$: C, 58.94; H, 5.24; Found: C, 58.62; H, 5.49

EXAMPLE 21

Preparation of 2,3,4,5-tetrahydro-7-hydroxy-7-phenyl-7H-diazepino[2,1-a]isoindole A solution of 10.5 g. of 2-benzoylbenzaldehyde and 28.5 ml. of 1,4-diaminobutane in 100 ml. of toluene was refluxed for 18 hours. During this time 2.5 ml. of an aqueous phase had separated in a Dean Stark receiver. The solution was exposed to air for 60 hours, concentrated and diluted with 300 ml. of carbon tetrachloride. A crystalline precipitate was obtained which was suspended in 40 ml. of ethanol. A solution of 1.9 g. of oxalic acid in 40 ml. of methanol was added and the solution was concentrated and diluted with ether. The precipitate was collected and recrystallized from a mixture of methanol and ether to give the oxalic acid salt as white prisms melting at ca. 200° dec. This salt was suspended in a mixture of aqueous sodium carbonate solution and methylene chloride. The methylene chloride solution was concentrated and the residue was recrystallized from a mixture of chloroform and ether to give the product as white needles melting at 216°–220° dec. Ultraviolet maxima (2-propanol) at 258 m$\mu$ ($\epsilon$ = 5000), 265 m$\mu$ ($\epsilon$ = 5100), 273 m$\mu$ ($\epsilon$ = 4800), inflexions at 230 m$\mu$ ($\epsilon$ = 15,000), 290 m$\mu$ ($\epsilon$ = 2400); infrared absorption (KBr) at 1650 cm$^{-1}$.

Anal. Calcd. for $C_{18}H_{18}N_2O$: C, 77.67; H, 6.52; O, 5.75; Found: C, 77.64; H, 6.75; O, 5.64

EXAMPLE 22

Preparation of 2-(2-aminoethyl)-3-phenylphthalimidine

A solution of 25 g. (0.1 mole) of 1,2,3,9b-tetrahydro-9b-phenyl-5H-imidazo[2,1-a]isoindol-5-one in 150 ml. of acetic acid containing 2.5 g. of hydrogen chloride was shaken under one atmosphere of hydrogen at 25° using 0.5 g. of platinum oxide as catalyst. In the course of 7 hours, 3000 ml. of hydrogen (theory ca. 2500 ml.) was absorbed and the rate of uptake had slowed down considerably. The solution was poured into ice water, basified with ammonia and extracted with methylene chloride. The organic phase was dried and concentrated. The residue crystallized with ether and after recrystallization from a mixture of methylene chloride and petroleum ether gave white prisms of 2-(2-aminoethyl)-3-phenylphthalimidine melting at 90°–93°. $\gamma_{CO}^{CHCl} = 1685$ cm$^{-1}$, $\lambda_{max}^{i-prop} = 247$ m$\mu$, $\epsilon = 6000$, 279 m$\mu$, $\epsilon = 1900$.

Anal. Calcd. for $C_{16}H_{16}N_2O$: C, 76.16; H, 6.39; Found: C, 75.81; H, 6.32

EXAMPLE 23

Preparation of 2-[2-(2-chlorobenzoyl)phenyl]-2-imidazoline

To 250 ml. of concentrated sulfuric acid was added, with stirring and slight cooling, 37.5 g. (0.545 mole) of sodium nitrite. To this was added 120.5 g. (0.50 mole) of 2-(2-aminobenzoyl)benzoic acid at such a rate that the temperature of the reaction mixture remained between 30°–40°. After the addition was complete the reaction mixture was stirred for one hour and then poured into one liter of ice and water and filtered. The filtrate was added rapidly to a stirred solution of 55 g. (0.555 mole) of cuprous chloride, 150 g. of sodium chloride, 250 ml. of concentrated hydrochloric acid and 300 ml. of water. The precipitated gum was extracted with chloroform and the extracts were washed twice with water, dried over anhydrous sodium sulfate and evaporated under vacuo to leave a red oil which crystallized upon scratching. Recrystallization from 200 ml. of ethyl acetate gave 2-(2-chlorobenzoyl)benzoic acid as a pink solid. A sample recrystallized three times from ethyl acetate gave colorless prisms, double m.p. 112°–116° and 124°–126°.

To a stirred suspension of 22.8 g. (0.60 mole) of lithium aluminum hydride in 700 ml. of dry tetrahydrofuran was added 104 g. (0.40 mole) of 2-(2-chlorobenzoyl)benzoic acid prepared as above in portions keeping the reaction mixture temperature between 15°–30° with ice cooling. After the addition was complete the reaction mixture was stirred for one hour. Ether (400 ml.) was added followed by the slow addition of 80 ml. of water, with ice cooling. The mixture was filtered through a large sintered glass funnel which contained a matting of Celite filter-aid. The filtered solids were washed with tetrahydrofuran and the combined filtrates were evaporated under vacuo to a yellow oil which crystallized upon scratching. The material was recrystallized from 150 ml. of isopropyl ether to give 2-chloro-2'-hydroxymethylbenzhydrol as a slightly pink solid, m.p. 85°–87°. A sample was recrystallized three times from isopropyl ether to give colorless prisms, m.p. 86°–87°.

A 2-liter, 3-necked, round bottomed flask was fitted with a mechanical stirrer, dropping funnel and a Dean-Stark trap fitted with a condenser. A mixture of 41.7 g. (0.376 mole) of selenium dioxide in 150 ml. of acetic acid and 300 ml. of xylene was refluxed for 15 minutes. To the boiling mixture was added dropwise during one hour, a solution of 74.4 g. (0.3 mole) of 2-chloro-2'-hydroxymethylbenzhydrol prepared as above in 85 ml. of acetic acid and 250 ml. of xylene. The Dean-Stark trap was cooled during this time to promote separation of an aqueous phase. About 60 ml. of the aqueous phase was separated during 5 hours. The reaction mixture was refluxed for a total of 22 hours, cooled and filtered. The filtrate was added to 800 ml. of ice and water, made alkaline with 50 percent sodium hydroxide and the mixture extracted with 600 ml. of ether. The extracts were washed with water, dried over anhydrous sodium sulfate and evaporated to yield an orange oil which could not be crystallized. Vapor phase chromatographic analysis showed the presence of two compounds. 45.4 Grams of the oil, 52.5 g. (0.875 mole) of ethylenediamine and 400 ml. of benzene were refluxed for 5 hours in a round bottomed flask equipped with a Dean-Stark trap and a condenser. About 6 ml. of aqueous phase separated in the trap. The reaction mixture was cooled, washed three times with saturated aqueous salt solution and dried over anhydrous sodium sulfate. Air was then bubbled through the benzene solution for 15 hours but only a small amount of solid separated.

The benzene was removed under vacuo and the residue was dissolved in 150 ml. of ethanol and 40 ml. (0.350 mole) of 30 percent hydrogen peroxide. After stirring for 3 hours the ethanol was removed under vacuo and 300 ml. of benzene was added to the residue. The aqueous phase was separated and the benzene solution was dried over anhydrous sodium sulfate and evaporated under vacuo to leave a pale yellow oil. Ether (150 ml.) was added and a crystalline solid separated. The mixture was filtered to give a pale yellow solid, m.p. 164°–167° dec. The ether filtrate was stirred at room temperature, exposed to air, for two days. The precipitated solid was filtered to give an additional pale yellow solid. Thin layer chromatography of the combined solids showed the presence of one major component, Rf 0.41, and a minor component, Rf 0.67. The latter component was 2,3-dihydro-5-hydroperoxy-5-(o-chlorophenyl)-5H-imidazo[2,1-a]isoindole since the yellow solid precipitated iodine from a saturated methanolic potassium iodide solution.

To a suspension of the yellow solid in 60 ml. of refluxing methanol was added a solution of 4.28 g. (0.017 mole) of $Na_2SO_3 \cdot 7H_2O$ in 30 ml. of water over a period of 5 minutes. After refluxing for 15 minutes longer the reaction mixture was cooled and filtered. The filtered solid was washed 3 times with 20 ml. of water and dried. Recrystallization from methanol-chloroform gave 2-[2-(2-chlorobenzoyl)phenyl]-2-imidazoline as colorless prisms, m.p. 180°–181° dec.

Anal. Calcd. for $C_{16}H_{13}ClN_2O$: C, 67.49; H, 4.60; N, 9.84; Found: C, 67.15; H, 4.56; N, 9.66

The 2-[2-(2-chlorobenzoyl)phenyl]-2-imidazoline prepared in this manner can form the isomeric 2,3-dihydro-5-hydroxy-5-(2'-chlorophenyl)-5H-imidazo[2,1-a]isoindole.

To a hot solution of 6.0 g. (21.2 mmoles) of 2-[2-(2-chlorobenzoyl)phenyl]-2-imidazoline in 25 ml. of 6 N methanolic hydrogen chloride and 35 ml. of methanol was added 200 ml. of ether and the solution cooled. Filtration gave 2-[2-(2-chlorobenzoyl)phenyl]-2-imidazoline hydrochloride, m.p. 178°–180° dec. Dilution of the mother liquors with 200 ml. of ether followed by cooling and filtering afforded an additional quantity of hydrochloride. Recrystallization from methanol-ether gave colorless prisms, m.p. 178°–180° dec.

Anal. Calcd. for $C_{16}H_{14}Cl_2N_2O$: Cl, 22.08; Found: Cl, 22.00

EXAMPLE 24

Preparation of 2-(2-benzoylphenyl)-2-imidazoline via 1,2,3,9b-tetrahydro-5H-imidazo[2,1-a]isoindol-5-one A solution of 7.5 g. of phthalaldehydic acid in 30 ml. of ethanol and 34 ml. of ethylenediamine was refluxed for 16 hours. The solution was concentrated in vacuo and the residue was dissolved in methylene chloride. The solution was washed with water, dried and concentrated. The residue was distilled in a bulb tube at 0.3 mm at a bath temperature of 150°–180°. A colorless oil was obtained which was dissolved in methanol and on addition of ethereal hydrogen chloride gave white prisms of 1,2,3,9b-tetrahydro-5H-imidazo[2,1-a]isoindol-5-one hydrochloride, m.p. 222°–224° dec.

The salt obtained in the preceding experiment was treated with aqueous potassium carbonate solution. Extraction with methylene chloride gave an oil of which 0.9 g. was dissolved in a mixture of 25 ml. of benzene and 10 ml. of ether. To this solution was added 5.5 ml. of a 2 N solution of phenyl lithium in a mixture of benzene and ether (7:3). After stirring at 25° for 1 hour the solution was poured into ice water and extracted with ethyl acetate. This solution was concentrated and the residue was exposed to air for 48 hours. On addition of methylene chloride crystals were obtained which were dissolved in methanol. Addition of ethereal hydrochloric acid gave white prisms which after recrystallization from a mixture of methanol and ether gave crystals melting at 173°–175° dec. This material was identical with authentic 2-(2-benzoylphenyl)-2-imidazoline hydrochloride.

We claim:
1. A compound of the formula

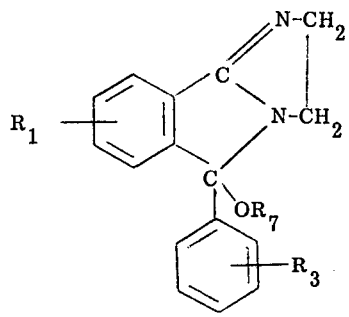

wherein $R_1$ and $R_3$ are each independently selected from the group consisting of hydrogen and halogen; and $R_7$ is lower alkyl
or a pharmaceutically acceptable acid addition salt thereof.

2. The compound according to claim 1 wherein $R_1$ and $R_3$ are each hydrogen, i.e., the compound 2,3-dihydro-5-methoxy-5-phenyl-5H-imidazo[2,1-a]isoindole.

* * * * *